United States Patent
den Hertog et al.

(10) Patent No.: US 10,508,095 B2
(45) Date of Patent: Dec. 17, 2019

(54) METHOD FOR PRODUCING ANTIBIOTIC FROM PLEOSPORACEAE ULOCLADIUM

(71) Applicant: Koninklijke Nederlandse Akademie van Wetenschappen, Amsterdam (NL)

(72) Inventors: Jeroen den Hertog, Bunnik (NL); Gisela Johanna van der Velden, Montfoort (NL); Jelmer Hoeksma, Utrecht (NL)

(73) Assignee: Koninklijke Nederlandse Akademie van Wetenschappen, Amsterdam (NL)

( * ) Notice: Subject to any disclaimer, the term of this patent is extended or adjusted under 35 U.S.C. 154(b) by 0 days.

(21) Appl. No.: 15/885,869

(22) Filed: Feb. 1, 2018

(65) Prior Publication Data

US 2019/0040033 A1   Feb. 7, 2019

Related U.S. Application Data

(62) Division of application No. 15/329,758, filed on Jan. 27, 2017, now Pat. No. 9,920,025.

(51) Int. Cl.
 *C07D 313/18* (2006.01)
(52) U.S. Cl.
 CPC .................. *C07D 313/18* (2013.01)
(58) Field of Classification Search
 None
 See application file for complete search history.

(56) References Cited

U.S. PATENT DOCUMENTS 9,756,865 B2 * 9/2017 Sword ...................... A01H 5/10
9,920,025 B2 * 3/2018 Den Hertog ......... C07D 313/18

OTHER PUBLICATIONS

Baratta et al., "Highly stereoselective formation of cis-enediones from alpha-diazo carbonyl compounds catalyzed by [RuCl([eta]5-C5H5)(PPh3)2]", Chemical Communications, 1997, pp. 2163-2164.
Boeckman et al., "Revised structure of vermiculine. A Novel macrolide dilactone antibiotic from Penicillium vermiculatum", Journal of the American Chemical Society, 1974, vol. 96, pp. 5954-5956.
He et al., "Isolation an antimicrobial action of endophytic fungi from sophora flavescens and effects on microorganism circumstances in soil", Procedia Environmental Sciences, 2013, vol. 18, pp. 264-270.
International Search Report issued in International Patent Application No. PCT/NL2015/050556 dated Oct. 27, 2015.

* cited by examiner

*Primary Examiner* — Ralph J Gitomer
(74) *Attorney, Agent, or Firm* — NLO; Catherine Shulz; Tamara Stegmann

(57) ABSTRACT

Fermentation processes that use fungi of the genus *Ulocladium* for producing novel compounds that include an 8- or 9-membered cyclic structure, wherein an (E)-1,4-dioxo-but-2-ene moiety is embedded in the cyclic structure. The compounds may be used as medicaments, in particular as medicaments for treating and preventing microbial infections, such as infections by multidrug resistant and/or Gram-positive bacteria.

4 Claims, 11 Drawing Sheets

METHOD FOR PRODUCING ANTIBIOTIC FROM PLEOSPORACEAE ULOCLADIUM

FIELD OF THE INVENTION

The present invention relates to the fields of medicine, microbiology and organic chemistry. In particular, the invention relates to a novel compound obtainable from a fungus that has antibiotic activity, methods for its production and for its use in treating microbial infections.

BACKGROUND OF THE INVENTION

Bacterial infection is a serious threat to human and animal life. Antibiotics have been developed that counter bacterial infection. The first antibiotic drug, Penicillin, was discovered in 1928 and turned out to be very effective in combating bacterial infections. Penicillin has literally saved millions of human lives. Many more antibiotics have been discovered since. However, resistance is emerging to existing antibiotics and increasing globalization is adding to the rapid spread of bacterial infections. So-called superbugs are emerging that are resistant to virtually all currently known antibiotics. These now form a serious threat to human life. Methicillin-resistant *Staphylococcus aureus*, or MRSA, the best known superbug, now kills more Americans each year than AIDS. In addition, extended-spectrum beta-lactamase (ESBL)-producing Enterobacteriaceae are resistant to most antibiotics. The first human death in The Netherlands resulting from infection with ESBL-producing bacteria was reported in 2010. Pathogenic *Streptococcus pneumoniae* and *Mycobacterium tuberculosis* are (re-)emerging as human disease-inducing agents as well.

Therefore, there is an increasing need in the art for novel antibiotics, preferably novel antibiotics that are useful for combating infection by bacteria that are resistant to most or all currently known antibiotics. It is an object of the present invention to provide such a novel antibiotic, methods for its production and for its use in treating bacterial infections.

DESCRIPTION OF THE INVENTION

In a first aspect, the invention pertains to novel compounds that contain a unique cyclic structure. In this context, it is referred to the "cyclic structure according to the invention".

The cyclic structure according to the invention preferably is an 8- or 9-membered ring, more preferably an 8-membered ring, which comprises an (E)-1,4-dioxo-but-2-ene moiety (a —C(O)—C=C—C(O)— moiety in trans conformation) embedded in the ring, i.e. the four carbon atoms are part of the ring. The presence of a carbon-carbon double bond in E-configuration adjacent to two further $sp^2$ carbon atoms within an 8- or 9-membered ring, in particular within an 8-membered ring, is unprecedented in the art.

The eight or nine atoms that form the ring of the cyclic structure are referred to as "ring atoms". By virtue of the (E)-1,4-dioxo-but-2-ene moiety, the cyclic structure contains at least four carbon ring atoms. The further four or five ring atoms are preferably selected from carbon, oxygen and nitrogen, more preferably from carbon and oxygen. Preferred ring systems have 0-3 oxygen ring atoms, more preferably 1-2 oxygen ring atoms, most preferably 1 oxygen ring atom, wherein the remaining ring atoms are carbon atoms. In case the cyclic structure is an 8-membered ring, the ring preferably contains seven carbon atoms and one oxygen atom. In case the cyclic structure is a 9-membered ring, the ring preferably contains eight carbon atoms and one oxygen atom.

According to a preferred embodiment, the cyclic structure according to the invention preferably has one oxygen ring atom and 7 or 8, preferably 7, carbon ring atoms. The oxygen is preferably located directly adjacent to one of the carbonyl moieties of the (E)-1,4-dioxo-but-2-ene moiety, wherein the cyclic structure thus is a lactone. Thus, the cyclic structure preferably comprises an (E)-4-oxo-but-2-enoate (a —C(O)—C=C—C(O)—O— moiety in trans conformation) embedded in the ring, i.e. the four carbon atoms and the singly-bonded oxygen atom are part of the ring. Lactonic cyclic structures according to the invention may be referred to as an (E)-7-hydroxy-4-oxo-hept-2-enoic acid lactone ring or as an (E)-8-hydroxy-4-oxo-oct-2-enoic acid lactone ring. Preferably, the cyclic structure is an (E)-7-hydroxy-4-oxo-hept-2-enoic acid lactone ring. Such a preferred cyclic structure may also be referred to as an (E)-7,8-dihydro-2H-oxocine-2,5(61H)-dione ring.

In the compound according to the invention, the cyclic structure may or may not be substituted. In the context of the present invention, hydrogen atoms are not regarded substituents. Substituents may be present on any atom available for substitution. In particular the ring atoms not part of the 1,4-dioxo-2-E-ethylene moiety may be substituted. Although the cyclic structure according to the invention is a single 8-membered or 9-membered ring, it may be part of a Spiro or fused ring system by virtue of such substituents, bridging one or two ring atoms of the cyclic structure.

Thus, in a preferred embodiment, the ring structure of the invention is unsubstituted or substituted with one or more substituents selected from halogen, alkyl, alkenyl, alkynyl, aryl, amino, hydroxyl, alkoxy, acyl, acyloxy, amino carbonyl, cyano and nitro, preferably from halogen and alkyl, more preferably with F or $(C_{1-3})$alkyl, most preferably with methyl. In a further preferred embodiment, the ring structure of the invention is unsubstituted or substituted with 1-3 substituents selected from halogen, alkyl, alkenyl, alkynyl, aryl, amino, hydroxyl, alkoxy, acyl, acyloxy, amino carbonyl, cyano and nitro, preferably from halogen and alkyl, more preferably with F or $(C_{1-3})$alkyl, most preferably with methyl. In a further preferred embodiment, the ring structure of the invention is substituted with 1-2 substituents selected from halogen, alkyl, alkenyl, alkynyl, aryl, amino, hydroxyl, alkoxy, acyl, acyloxy, amino carbonyl, cyano and nitro, preferably from halogen and alkyl, more preferably with F or $(C_{1-3})$alkyl, most preferably with methyl. In an further preferred embodiment, the ring structure of the invention is substituted with 1 substituents selected from halogen, alkyl, alkenyl, alkynyl, aryl, amino, hydroxyl, alkoxy, acyl, acyloxy, amino carbonyl, cyano and nitro, preferably from halogen and alkyl, more preferably with F or $(C_{1-3})$alkyl, most preferably with methyl.

Herein, "amino" refers to a primary amine moiety ($NH_2$), a secondary amino moiety (alkylamino) and a tertiary amino moiety (dialkylamino). Herein, the term "alkyl" refers to aliphatic unsaturated moieties including straight-chain alkyl groups, branched-chain alkyl groups, cyclic alkyl groups, and combinations thereof, having the number of carbon atoms specified, or if no number is specified, preferably having up to 12 carbon atoms, more preferably up to 6 carbon atoms. This definition also applies to the alkane radicals present in alkylamino, dialkylamino, alkoxy, acyl and acyloxy moieties. Likewise, the terms "alkenyl" and "alkynyl" refer to alkyl moieties as defined above containing at least one carbon-carbon double bond or at least one carbon-carbon triple bond, respectively, preferably having up to 12 carbon atoms, more preferably up to 6 carbon atoms.

Preferred compounds according to the invention have a cyclic structure being a (E)-7-hydroxy-4-oxo-hept-2-enoic acid lactone ring or a (E)-8-hydroxy-4-oxo-oct-2-enoic acid lactone ring, which are substituted with 1 substituents being ($C_{1-3}$)alkyl, preferably being methyl. All other valencies on the carbon ring atoms are thus occupied by hydrogen atoms. Preferably, said methyl substituent is located at the carbon ring atom next to the oxygen ring atom of the lactone group. According to the most preferred embodiment, the compound according to the invention is (E)-7-hydroxy-4-oxo-oct-2-enoic acid lactone, which may also be referred to as (E)-8-methyl-7,8-dihydro-2H-oxocine-2,5(6H)-dione, i.e. a compound according to formula (I) herein.

In one embodiment, the cyclic structure according to the invention is not substituted with an acetyl moiety, in particular the compound according to the invention is not (E)-8-hydroxy-4,9-dioxo-dec-2-enoic acid lactone. In one embodiment, the cyclic structure according to the invention is not an eight-membered ring with eight carbon ring atoms, in particular the compound according to the invention is not trans-2-cyclooctene-1,4-dione.

The present invention also relates to salts, esters and prodrugs of the compounds according to the invention, preferably pharmaceutically acceptable salts, esters and prodrugs of the compounds and more preferably pharmaceutically acceptable salts of the compounds.

Preferably, the compound according to the invention is in isolated form or present in a composition comprising at least 38, 40, 50, 100, 200, 500 or 1,000 ppm (w/w) or at least 0.2, 0.5, 1.0, 2.0, 5.0 or 10.0% (w/w) of the compound according to the invention, based on dry weight. More preferably, the compound according to the invention is in isolated form. The compounds according to the invention may be obtained by synthesis or by isolation from natural sources, e.g. as (secondary) metabolite from *Ulocladium lanuginosum* (available as CBS 102.26).

Preferably the compound of the invention has antimicrobial or antibiotic activity, more preferably antibacterial activity. Antimicrobial or antibacterial activity can be assessed by a suitable assay known by the person skilled in the art, preferably by a growth inhibition assay as exemplified herein. Preferably growth inhibition is assessed by culturing bacteria are cultured in the presence or absence of the antibacterial compound o/n at 37° C. in Luria Broth (LB). The read-out of the assay is by eye, if the bacteria have visibly grown, the sample is scored as non-inhibitory. If the broth is completely clear, the sample is scored as inhibitory.

Also preferred is a growth kinetic assay the effect of the compound of interest is assessed in time on growth of bacterial isolates on blood-agar plates, as known by the person skilled in the art. In brief, liquid cultures are inoculated in Mueller-Hinton Broth and incubated at 37° C. o/n. The o/n cultures were used to prepare a 0.05-0.1 McFarland suspension in Mueller Hinton Broth, which are incubated at 37° C. until 0.5 McFarland (~1×10$^6$ CFU/ml). These suspensions are used to inoculate 5 ml pre-warmed Mueller-Hinton Broth with approximately 1.5×10$^5$ CFU/ml with the appropriate antibiotic compound of interest. Directly after addition of the bacterial suspension a 0.25 ml sample is taken. Further 0.25 ml samples are taken after 1, 3, 6 and 24 hrs, which are added to 2.25 ml physiological salt solution. This suspension is used to prepare plates for CFU determination. The lower limit of detection is 40 CFU/ml. Bacterial suspension without antibiotics is preferably checked for normal growth after 24 hrs. A compound is understood herein as having antibacterial activity if at least 3 $\log_{10}$ reduction of CFU in the growth kinetics assay as assed after 1, 3, 6 or preferably 24 hours.

Preferably, the compound of the invention has antibacterial activity against Gram-positive bacteria, more preferably bacteria that belong to a genus selected from the group consisting of *Streptococcus, Staphylococcus, Corynebacterium, Listeria, Bacillus, Enterococcus* and *Clostridium*, or, more specifically, bacteria that belong to a species selected from the group consisting of *Streptococcus agalactiae, Streptococcus pneumonia, Streptococcus pyogenes, Staphylococcus aureus, Staphylococcus epidermidis, Staphylococcus saprophyticus, Corynebacterium diphtheria, Listeria monocytogenes, Enterococcus faecalis, Enterococcus faecium, Bacillus anthracis, Bacillus cereus, Clostridium botulinum, Clostridium difficile, Clostridium perfringens,* and *Clostridium tetani* as assessed in an assay as defined herein. Even more preferably, the compound of the invention has antibacterial activity against the strains *Staphylococcus epidermidis* (08A1071), Methicillin-sensitive *Staphylococcus aureus* 476 (S0101) (available from the ATCC under number BAA-1721), Methicillin-resistant *Staphylococcus aureus* (MRSA) ST8:USA300 (S1474) (available from the Network on Antimicrobial Resistance in *Staphylococcus aureus* (NARSA; www.narsa.net) collection under number NRS482), *Enterococcus faecium* (15A623), *Enterococcus faecium* (16D030), *Streptococcus* group A (23M092), *Streptococcus* group B (05A396), *Streptococcus pneumoniae* (14B186), and *Listeria monocytogenes* (41-4a), preferably against at least 2, 3, 4, 5, 6, 7, 8 or all of these strains, as assessed in an assay as defined herein. Most preferably, the compound of the invention has antibacterial activity against a methicillin-resistant *Staphylococcus*, preferably a methicillin-resistant *Staphylococcus aureus*. Even more preferably, the compound of the invention has antibacterial activity against methicillin-resistant *Staphylococcus aureus* strain ST8:USA300 (S1474), as assessed in an assay as defined herein.

Preferably, a compound is understood herein as having antibacterial activity if a sample comprising at most 200 µg/ml, 150 µg/ml, 100 µg/ml, 75 µg/ml 50 µg/ml, 25 µg/ml, 10 µg/ml, 5 µg/ml, 4.7 µg/ml, or preferably at most 1 µg/ml of the compound is scored in an assay as defined herein when using a bacterium as defined herein. More preferably, a compound is understood herein as having antibacterial activity if the compound has at least 30%, 40%, 50%, 60%, 70%, 80%, 90% or preferably 100% of the activity of the compound of Formula I, as assessed in an assay as defined herein using a bacterium as defined herein.

In a preferred embodiment, the compound of the invention has antibacterial activity against gram-positive bacteria as defined above, wherein said compound does not show any antibacterial activity against Gram-negative bacteria, as assessed in an assay as defined herein. Preferably, the compound of the invention has no antibacterial activity against bacteria that belong to a genus selected from *Acinetobacter, Actinobacillus, Bordetella, Brucella, Campylobacter, Cyanobacteria, Enterobacter, Erwinia, Escherichia coli, Franciscella, Helicobacter, Hemophilus, Klebsiella, Legionella, Moraxella, Neisseria, Pasteurella, Proteus, Pseudomonas, Salmonella, Serratia, Shigella, Treponema, Vibrio* and *Yersinia*, or, more specifically, bacteria that belong to the species selected from *Klebsiella pneumoniae* (MR44), *Acinetobacter calcoaceticus* (15A600), *Pseudomonas aeruginosa, Stenotrophomonas maltophilia, Klebsiella pneumonia, Klebsiella pneumonia,*

*Klebsiella pneumonia, Escherichia coli, Escherichia coli* and *Escherichia coli*, as assessed in an assay as defined herein. More preferably, the compound of the invention does not have antibacterial activity against a strain selected from the group consisting of *Klebsiella pneumoniae* (MR44), *Acinetobacter calcoaceticus* (15A600) (available from The Netherlands Culture Collection of Bacteria (NCCB) under number NCCB 100514), *Pseudomonas aeruginosa* (04A191) (available from the NCCB under number NCCB 100515), *Stenotrophomonas maltophilia* (20A226) (available from the NCCB under number NCCB 100516), *Klebsiella pneumonia* (CP14), *Klebsiella pneumonia* (J5006), *Klebsiella pneumonia* (J5264), *Escherichia coli* (J5004), *Escherichia coli* (CP131), *Escherichia coli* (J5203), preferably the compound has no antibacterial activity against at least 2, 3, 4, 5, 6, 7, 8, 9 or all of these strains, as assessed in an assay as defined herein.

Preferably, a compound is understood herein as having no antibacterial activity if a sample comprising at least 1 µg/ml, 4.7 µg/ml, 5 µg/ml, 10 µg/ml, 25 µg/ml 50 µg/ml, 75 µg/ml, 100 µg/ml, 150 µg/ml preferably at least 200 µg/ml of the compound is scored an assay as defined herein as non-inhibitory when using a bacterium as defined herein, as assed in an say as defined herein. More preferably, a compound is understood herein as having no antibacterial activity if the compound has no more than 100%, 90%, 80%, 70%, 60%, 50% or preferably 40% of the activity of the compound of Formula I, as assessed in an assay as defined herein using a bacterium as defined herein.

In a second aspect, the invention relates to a pharmaceutical composition comprising a compound according to the invention as an active ingredient. An active ingredient is to be understood herein as an ingredient that has antibiotic activity, more preferably antibacterial activity as defined herein above.

The pharmaceutical composition preferably further comprises a pharmaceutically acceptable carrier, excipient and/or vehicle, in addition to the active ingredient. Thus, the compounds according to the invention can be formulated as pharmaceutical or compositions by formulation with additives such as pharmaceutically or physiologically acceptable excipients, carriers, and vehicles. Suitable pharmaceutically or physiologically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-P-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21" edition (2005), incorporated herein by reference.

A pharmaceutical or composition can comprise a unit dose formulation, where the unit dose is a dose sufficient to have a therapeutic effect. The unit dose may be sufficient as a single dose to have a therapeutic effect. Alternatively, the unit dose may be a dose administered periodically in a course of treatment of an infectious disease.

Pharmaceutical compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly (imidocarbonates) and poly(phosphazenes).

The compounds of the invention may be administered enterally, orally, parenterally, sublingually, by inhalation (e. g. as mists or sprays), rectally, or topically in dosage unit formulations containing conventional nontoxic pharmaceutically or physiologically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e. g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The compounds are mixed with pharmaceutically acceptable carriers, adjuvants, and vehicles appropriate for the desired route of administration. Oral administration is a preferred route of administration, and formulations suitable for oral administration are preferred formulations. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at room temperature but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., Methods in Cell Biology, Volume XIV, Academic Press, New York, N.Y., p. 33 et seq (1976).

The compound according to the invention is administered in a therapeutically effective amount, which will vary depending upon a variety of factors including the activity of the specific pharmaceutical composition employed; the metabolic stability and length of action of the composition; the age, body weight, general health, sex, and diet of the patient; the mode and time of administration; the rate of excretion; the drug combination; the severity of the particular disorder or condition; and the subject undergoing therapy. Generally, a therapeutically effective daily dose is from about 0.001 mg/kg to about 100 mg/kg, preferably, from about 0.01 mg/kg to about 50 mg/kg, more preferably from about 1 mg/kg to about 25 mg/kg.

For veterinary use, the dose is generally in the range of from 1 to 200 mg, and preferably from 5 to 100 mg, per kg of body weight per day while varying depending on the purpose of administration (for therapy or for prevention), the kind and the size of the animal, the kind of the pathogenic organisms, and severity of symptom.

A pharmaceutical composition of the invention intended e.g. for parenteral or oral administration should contain an amount of a compound of the invention such that a suitable dosage will be obtained. Typically, the amount of the compound is at least 0.01% of a pharmaceutical composition of the invention. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 10% by weight of the compound of the invention prior to dilution.

In a third aspect, the invention relates to a compound according to the invention, or a pharmaceutical composition comprising a compound according to the invention as active ingredient, for use as a medicament. The medicament can be a medicament for both human and veterinary purposes.

In a fourth aspect, the invention relates to a compound according to the invention, or a pharmaceutical composition comprising a compound according to the invention as active ingredient, for use in treating a microbial infection. Preferably, the compound or composition is for use in treating or preventing a microbial infection in a human or animal subject. The microbial infection preferably is a bacterial infection. In an alternative embodiment, the compound according to the invention, or a composition comprising a compound according to the invention is used in cosmetic or non-therapeutic method for treating or preventing microbial infections and/or for disinfection human or animal subjects and body parts thereof. Accordingly, the above described pharmaceutical compositions comprising a compound according to the invention as active ingredient can thus also be or used as cosmetic compositions or disinfectants.

In one embodiment, the compound according to the invention, or the pharmaceutical composition comprising the compound according to the invention as active ingredient is used for treating or preventing an infection by a multidrug resistant bacterium. A multidrug resistant bacterium is herein understood as a bacterial strain that is resistant to more than one type of antibiotic and that are therefore more difficult, if not impossible to treat. Notorious examples of multidrug resistant bacteria include e.g. methicillin-resistant *Staphylococcus aureus* (MRSA) and extended-spectrum beta-lactamase (ESBL)-producing Enterobacteriaceae.

In a preferred embodiment, the compound according to the invention, or the pharmaceutical composition comprising the compound according to the invention as active ingredient is used for treating or preventing an infection by a Gram-positive bacterium, in a particular a pathogenic Gram-positive bacterium. Infections by Gram-positive bacteria that can be treated and/or prevented using a compound or composition according to the invention include infections by bacteria that belong a genus selected from *Streptococcus, Staphylococcus, Corynebacterium, Listeria, Bacillus, Enterococcus* and *Clostridium*, or, more specifically, bacteria that belong to the species selected from *Streptococcus agalactiae, Streptococcus pneumonia, Streptococcus pyogenes, Staphylococcus aureus, Staphylococcus epidermidis, Staphylococcus saprophyticus, Corynebacterium diphthe-* ria, *Listeria monocytogenes, Enterococcus faecalis, Enterococcus faecium, Bacillus anthracis, Bacillus cereus, Clostridium botulinum, Clostridium difficile, Clostridium perfringens*, and *Clostridium tetani*. Good results are obtained when the compound or composition according to the invention is used for treating and/or preventing an infection by a methicillin-resistant *Staphylococcus*, preferably a methicillin-resistant *Staphylococcus aureus*.

In an alternative embodiment, the compound according to the invention, or the pharmaceutical composition comprising the compound according to the invention as active ingredient is used for treating and/or preventing an infection by a *Mycobacterium* or a *Mycoplasma*, such as e.g. *Mycobacterium leprae, Mycobacterium tuberculosis, Mycobacterium ulcerans* and *Mycoplasma pneumonia*.

In a fifth aspect, the invention pertains to a method for treating a subject with a microbial infectious disease, the method comprising administering to the subject an effective amount of a compound according to the invention, or a pharmaceutical composition comprising a compound according to the invention as active ingredient. The subject can be human or animal subject suffering from a microbial infection. The microbial infection can be an infection by a bacterium as herein defined above.

A compound according to the invention, or a pharmaceutical composition comprising a compound according to the invention as active ingredient compound can be used in methods for the treatment or prevention of an microbial infection or disease selected from, for example, bacterial infection of wounds including surgical wounds, lung infections (e.g. tuberculosis), skin infections, and systemic bacterial infections. For instance, diseases which can be treated or prevented by the antimicrobial compounds of the present invention include, but are not limited to, anthrax, food poisoning, folliculitis, furuncle, carbuncle, erysipelas, phlegmon, lymphangitis/lymphadenitis, felon, subcutaneous abscess, spiradenitis, acne agminata, infectious atheroma, perianal abscess, masitadenitis, superficial secondary infections after trauma, burn or surgery trauma, pharyngolaryngitis, acute bronchitis, tonsillitis, chronic bronchitis, bronchiectasis, diffuse panbronchiolitis, secondary infections of chronic respiratory diseases, pneumonia, pyelonephritis, cystitis, prostatitis, epididymitis, urethritis, cholecystitis, cholangitis, bacillary dysentery, enteritis, adnexitis, intrauterine infections, bartholinitis, blepharitis, hordeolum, dacryocystitis, tarsadenitis, keratohelcosis, otitis media, sinusitis, paradentosis, pericoronitis, gnathitis, peritonitis, endocarditis, septicemia, meningitis, and skin infections.

In a sixth aspect, the invention relates to an antimicrobial composition, preferably a disinfectant, comprising a compound according to the invention as active ingredient. A disinfectant is an antimicrobial agent specific for use on inanimate objects. The antimicrobial composition or disinfectant of the invention may be in the liquid, solid or semi-liquid or semi-solid form. Preferably said antimicrobial composition or disinfectant is for controlling a Gram-positive bacterium, in a particular a pathogenic Gram-positive bacterium. Preferably the gram-positive bacterium belongs to a genus selected from *Streptococcus, Staphylococcus, Corynebacterium, Listeria, Bacillus, Enterococcus* and *Clostridium*, or, more specifically, to the species selected from *Streptococcus agalactiae, Streptococcus pneumonia, Streptococcus pyogenes, Staphylococcus aureus, Staphylococcus epidermidis, Staphylococcus saprophyticus, Corynebacterium diphtheria, Listeria monocytogenes, Enterococcus faecalis, Enterococcus faecium, Bacillus anthracis, Bacillus cereus, Clostridium botulinum, Clostridium difficile, Clostridium perfringens*, and *Clostridium tetani*. Most preferably, the methicillin-resistant *Staphylococcus*, preferably a methicillin-resistant *Staphylococcus aureus*.

Preferably, antimicrobial composition or disinfectant according to the sixth aspect or a pharmaceutical composition of the second aspect further comprises a pharmaceutical acceptable carrier and/or an additional active ingredient selected from the group consisting of a bacteriophage, a bacteriostatic agent, a bactericide agent, an antibiotic, a surfactant and/or an enzyme. An antibiotic of the present invention can be any antibiotic known in the art including antibiotics and chemotherapeutic agents, and including but not limited to vancomycin, nisin, danofloxacin and neomycin. An enzyme useful in a antimicrobial composition of the present invention includes but is not limited to enzymes that aid in breaking up biofims (e.g. biofilms found in processing and/or medical equipment) such as but not limited to polysaccharide depolymerise enzymes and protease. A surfactant useful in a composition of the present invention helps to wet the surface so that the active ingredient of the present invention, including the compound of the present invention, is properly distributed over the various surfaces, and to solubilise and remove dirt so that the microbes, preferably bacteria are accessible to the active ingredients of the invention. Suitable surfactants include but are not limited to polysorbate (tween) 80, 20 and 81 and Dobanols (Shell Chemical Co.®). An antimicrobial composition or disinfectant of the present invention may further comprise surface disinfectants known in the art such as but not limited to benzoic acid and PBT, preferably surface disinfectants with which a compound of the first aspect of the present invention is compatible.

In a seventh aspect, the present invention provides a use of a compound according to the first aspect, or an antimicrobial composition according to the sixth aspect present invention as an antimicrobial agent, preferably a disinfectant. Preferably the antimicrobial composition or disinfectant is for controlling a Gram-positive bacterium, in a particular a pathogenic Gram-positive bacterium. Preferably the gram-positive bacterium belongs to a genus selected from *Streptococcus, Staphylococcus, Corynebacterium, Listeria, Bacillus, Enterococcus* and *Clostridium*, or, more specifically, to the species selected from *Streptococcus agalactiae, Streptococcus pneumonia, Streptococcus pyogenes, Staphylococcus aureus, Staphylococcus epidermidis, Staphylococcus saprophyticus, Corynebacterium diphtheria, Listeria monocytogenes, Enterococcus faecalis, Enterococcus faecium, Bacillus anthracis, Bacillus cereus, Clostridium botulinum, Clostridium difficile, Clostridium perfringens*, and *Clostridium tetani*. Most preferably, the methicillin-resistant *Staphylococcus*, preferably a methicillin-resistant *Staphylococcus aureus*.

In an eighth aspect, the present invention provides a method for controlling microbial contamination in processing equipment or medical equipment comprising contacting a compound according to the first aspect of the present invention or a composition according the sixth aspect of the present invention with the processing equipment or medical equipment. Preferably a method according to the present invention is for controlling a Gram-positive bacterium, in a particular a pathogenic Gram-positive bacterium. Preferably the gram-positive bacterium belongs to a genus selected from *Streptococcus, Staphylococcus, Corynebacterium, Listeria, Bacillus, Enterococcus* and *Clostridium*, or, more specifically, to the species selected from *Streptococcus agalactiae, Streptococcus pneumonia, Streptococcus pyogenes*, Staphylococcus aureus, Staphylococcus epidermidis, Staphylococcus saprophyticus, Corynebacterium diphtheria, Listeria monocytogenes, Enterococcus faecalis, Enterococcus faecium, Bacillus anthracis, Bacillus cereus, Clostridium botulinum, Clostridium difficile, Clostridium perfringens, and Clostridium tetani. Most preferably, the methicillin-resistant Staphylococcus, preferably a methicillin-resistant Staphylococcus aureus.

Preferably, said method of controlling includes the reduction of counts of such bacteria and/or the prevention of their growth in the first place, on processing or medical equipment. Preferably, said method is of controlling for cleaning and sterilizing medical equipement, such as fiberscopes, like gastrocameras, peritoneoscopes, thoracoscopes and arthoroscopes, and medical supplies, like catheters and tubes that have long ducts or hollow portions and tend to be repetitively employed by being introduced into human bodies. A method of the present invention encompasses the application of compound according to the first aspect or a compositions according to the sixth aspect of the present invention on various physical sites on processing or medical equipment, by a number of means including, but not limited to, admixing, spraying or directly applying said compound according to the first aspect or a compositions according to the sixth aspect of the present invention. Optionally, the method of the present invention can be combined with any sterilization method or disinfectant known in the art such as ultrasonic cleaning, irradiation or thermal sterilization, by immersing the equipment in a disinfectant solution such as ethanol, ammonium, iodine and/or aldehyde disinfectant, or by using gas sterilization by retaining the device in a closed atmosphere such as formaline gas or ethylene oxide gas.

In a ninth aspect, the invention relates to methods for producing a compound according to the first aspect of the invention. A method for producing a compound of the preferably comprises the steps of a) culturing a fungus of the fungal Family of Pleosporaceae in a medium, and preferably under conditions, conducive to the production of the compound, and b) optionally, recovery of the compound. Preferably, the fungus of the fungal Family of Pleosporaceae is a fungus that produces a compound according to the invention. A fungus producing a compound according to the invention is herein understood as a fungus which, when grown in a standard medium for culturing fungi (e.g. Czapek-dox broth (CDB)+0.5% yeast extract), produces in the medium a compound with one or more of the characteristics: a) the compound has antimicrobial activity in an assay as herein defined above; b) the compound can be extracted from the medium using ethyl acetate; c) the compound has a molecular mass of around 154.05; d) the compound has a UV maximal absorbance 221 nm; and other characteristic defined herein or determined in the Examples herein.

Preferably, the fungus is a fungus that belong to the genus Ulocladium, more preferably, the fungus is a fungus of the species Ulocladium lanuginosum, and most preferably the fungus is the Ulocladium lanuginosum strain CBS 102.26, or strains derived from these fungi, e.g. by genetic modification and/or mutagenesis and selection.

The medium for culturing the fungus is a medium comprising at least a suitable carbon source and further comprising further nutrients and ingredient that support growth of the fungus. Suitable media for fermentation of fungi are well known in the art per se. Suitable carbon sources include e.g. glucose, syrups, dextrin, sucrose, starch, molasses and the like can be used. The medium will further usually include a nitrogen source such as e.g. soybean flour, wheat germ, corn-steep liquor, cottonseed cake, meat extract, peptone, yeast extract, ammonium sulfate, sodium nitrate, urea, and the like. Further medium components may be inorganic salts capable of yielding sodium, potassium, calcium, magnesium, cobalt, chloric, phosphoric, sulfuric and like ions.

In step a) of the method the fungus preferably ferments (at least part of) the carbon source to the compound according to the invention. Preferably the fungus is cultured in step a) at a temperature less than 30, 29, 28, 27, 26 or 25° C. More preferably, the fermentation (in step a) is performed at a temperature of no more than 24, 23, 22 or 21° C. and which is at least 15, 16, 17, 18 or 19° C. Most preferably the temperature is around 20° C. The fermentation preferably is an aerobic fermentation, especially a submerged aerobic fermentation is preferred.

The process for producing the compound of the invention further preferably comprises a step b) wherein the compound is recovered, purified and/or isolated. The compound is preferably recovered from medium by solvent extraction, optionally after removal of biomass from the medium. A skilled person will know suitable organic solvents for extraction of the compound from the medium and/or from the separated mycelium, such as e.g. ethyl acetate, chloroform, dichloromethane, ether, ethyl acetate, butyl acetate, methanol, ethanol, propanol, butanol or combinations thereof. A preferred solvent for solvent extraction is ethyl acetate. After concentration of the extracts the compound of the invention can be further purified and isolated e.g. by using usual chromatographic adsorbents or carrier materials.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

Growth of Fungi

Figure 1:
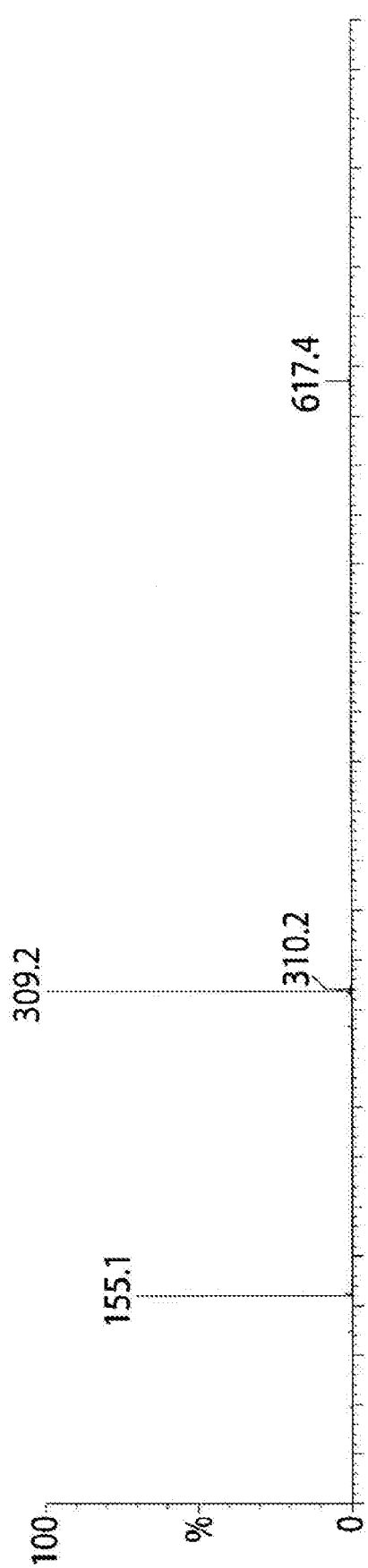
FIG. 1: MS/MS spectrum of the compound of formula (I), showing fragments of 155.1 (M+H), 309.2 (2M+H) and 617.4 (4M+H).

The fungus *Ulocladium lanuginosum*, strain CBS 102.26 (obtainable from Centraalbureau voor Schimmelcultures, Utrecht, The Netherlands; www.cbs.knaw.nl) was cultured on a malt-extract agar plate for 7 days at 25° C. The fungus was subsequently inoculated in 3 flasks containing 50 ml Czapek-dox broth (CDB)+0.5% yeast extract. Each flask was incubated at a different temperature—room temperature (RT), 25° C. or 30° C.—for 7 days. After 7 days, the fungal media were filter-sterilized (0.45 μm pore filter). A 1 ml aliquot of the filtrate was made and the rest of the filtrate was extracted 3× with ethyl acetate (EtOAc). The EtOAc was evaporated with a rotation evaporator and the residue was dissolved in 1 ml 5% DMSO in $H_2O$. The filtrates and extracts were tested on Methicillin resistant *Staphylococcus aureus* (MRSA; porcine strain) in broth as follows.

Antibiotic Assay

Bacteria are cultured o/n at 37° C. in Luria Broth (LB). This culture is diluted 100× in fresh LB. This fresh culture is then used to test the filtrate and extract. The filtrate was tested in serial dilutions starting at 2× and further diluted with a factor 2 until 256×. The extract was tested starting at 10× dilution and further diluted with a factor 2 until 1280×. The bacteria with filtrate or extract were incubated o/n at 37° C. The read-out of the assay is by eye, if the bacteria have visibly grown, the sample is scored as non-inhibitory. If the broth is completely clear, the sample is scored as inhibitory. Using this assay, we established that the extract from fungi grown at RT inhibited growth. The extract from fungi grown at 25° C. was less potent and the extract from fungi at 30° C. had no effect.

Purification of Compounds with Antibiotic Activity

Based on the first results, 20 jars of 50 ml CDB+0.5% yeast extract were inoculated with fungus *Ulocladium lanuginosum* CBS 102.26 and incubated at RT for 7 days. The medium was filter sterilized as described, a 1 ml aliquot was made of the filtrate, to be able to test the starting material, and the remainder was extracted 3× with EtOAc. The EtOAc was evaporated and the residue was dissolved in 1 ml DMSO. The extract was then fractionated using a C18 Reprosil column on a Prep. HPLC (see Table 4 for apparatus information) with UV-detection between 214 nm and 254 nm. The buffers used are described in Table 1, the buffer B gradient runs as described in Table 2.

TABLE 1

| HPLC buffers | |
| --- | --- |
| Buffer A | Buffer B |
| 95% MiliQ | 5% MiliQ |
| 5% Acetonitrile | 95% Acetonitrile |
| 0.1% Trifluoroacetic Acid | 0.1% Trifluoroacetic Acid |

TABLE 2

| HPLC gradient | |
| --- | --- |
| Time (min.) | Percentage buffer B |
| 0-5 | 0 |
| 5-85 | 0-100 |
| 85-90 | 100 |
| 90-95 | 100-0 |
| 95-100 | 0 |

The 95 fractions collected were pooled per 6 and the pooled fractions were dried in a speed-vac o/n. The fraction residues were dissolved in 1 ml 5% DMSO and tested on *E. faecium* (15A623) in serial dilutions starting at 2×. Pooled fraction 9 was the only one that inhibited bacterial growth, so the individual fractions in pooled fraction 9 (fractions 49-54) were tested further. 1 ml of each fraction was dried in a speed-vac o/n and each fraction residue was dissolved in 1 ml 5% DMSO to be tested on *E. faecium*. Fraction 49 was the only fraction that inhibited bacterial growth, which concurs with the UV detection of the HPLC fractionation (data not shown). The fraction was then tested on 19 additional strains of bacteria (Table 3). The filtrate and extract were found to inhibit the Gram-positive bacteria, but not the Gram-negative bacteria.

Identification of the Compound with Antibiotic Activity

The sample was run on analytical HPLC (see Table 4 for apparatus information), which indicated the compound was >95% pure (data not shown). An aliquot of fraction 49 was analyzed using LC-MS (see Table 4 for apparatus information) and high resolution mass spectrometry. The calculated mono-isotopic mass was 308.1067 with a molecular formula prediction of $C_{16}H_{20}O_6$. However, the MS/MS spectrum measured with the high resolution MS suggested that the calculated mass was actually 2M. The spectrum shows peaks at 155.1 (representing M+H), 309.2 (representing 2M+H) and 617.4 (representing 4M+H) (FIG. 1), suggesting that the exact mass is actually 154.05 (M) with molecular formula $C_8H_{10}O_3$. UV-VIS was also measured, revealing a UV-max at 221 nm (data not shown).

TABLE 3

| Antibiotic activity of purified fraction on different strains of bacteria | | | |
| --- | --- | --- | --- |
| Bacterium | ESBL* | Gram + or − | Minimal concentration for antibacterial activity |
| *Staphylococcus epidermidis* (08A1071) | — | Gram+ | 18.8 mg/l |
| Methicillin-sensitive *Staphylococcus aureus* 476 (S0101), ATCC BAA-1721 | — | Gram+ | 4.69 mg/l |

TABLE 3-continued

Antibiotic activity of purified fraction on different strains of bacteria

| Bacterium | ESBL* | Gram + or − | Minimal concentration for antibacterial activity |
|---|---|---|---|
| Methicillin-resistant *Staphylococcus aureus* (MRSA) ST8: USA300 (S1474) FPR3757, NARSA collection NRS482 | — | Gram+ | 18.8 mg/l |
| *Enterococcus faecium* (15A623) | — | Gram+ | 37.5 mg/l |
| *Enterococcus faecium* (16D030) | — | Gram+ | 75.0 mg/l |
| *Streptococcus group A* (23M092) | — | Gram+ | 75.0 mg/l |
| *Streptococcus group B* (05A396) | — | Gram+ | 75.0 mg/l |
| *Streptococcus pneumoniae* (14B186) | — | Gram+ | 75.0 mg/l |
| *Listeria monocytogenes* (41-4a) | — | Gram+ | 75.0 mg/l |
| *Klebsiella pneumoniae* (MR44) | — | Gram− | No effect at 1.5 g/l |
| *Acinetobacter calcoaceticus* (15A600), NCCB 100514 | — | Gram− | No effect at 1.5 g/l |
| *Pseudomonas aeruginosa* (04A191), NCCB 100515 | — | Gram− | No effect at 1.5 g/l |
| *Stenotrophomonas maltophilia* (20A226), NCCB 100516 | — | Gram− | No effect at 1.5 g/l |
| *Klebsiella pneumonia* (CP14) | TEM-18 | Gram− | No effect at 1.5 g/l |
| *Klebsiella pneumonia* (JS006) | SHV-18 | Gram− | No effect at 1.5 g/l |
| *Klebsiella pneumonia* (JS264) | CTX-M-15 | Gram− | No effect at 1.5 g/l |
| *Escherichia coli* (JS004) | TEM-3 | Gram− | No effect at 1.5 g/l |
| *Escherichia coli* (CP131) | SHV-3 | Gram− | No effect at 1.5 g/l |
| *Escherichia coli* (JS203) | CTX-M-1 | Gram− | No effect at 1.5 g/l |

*Extended-spectrum beta-lactamase

Elucidation of the Structure of the Bioactive Compound

The entire fraction 49 was subsequently evaporated in the speed-vac and the residue was dissolved in 400 μl DMSO-d6. The yield of the fraction was ~15 mg dry weight (from 1 L fungal culture). A $^1$H-NMR spectrum and a $^{13}$C-NMR spectrum were measured. The $^{13}$C-NMR spectrum revealed 8 carbon atoms, which together with the mono-isotopic mass measurements confirmed the calculated mono-isotopic mass of 154.0534 with molecular formula $C_8H_{10}O_3$. We then went on to perform several 2D-NMR experiments, namely Correlation Spectroscopy (COSY), Total Correlation Spectroscopy (TOCSY), Heteronuclear Single-Quantum Correlation Spectroscopy (HSQC), Heteronuclear Multiple-Bond Correlation spectroscopy (HMBC) and a $^{13}$C-Distortionless Enhancement by Polarization Transfer ($^{13}$C-DEPT). The NMR data (not shown) led us to the structure (E)-8-methyl-7,8-dihydro-2H-oxocine-2,5(6H)-dione, i.e. the structure formula (I):

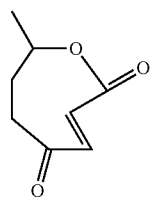

(I)

Formula (II) depicts the structure of (Z)-8-methyl-7,8-dihydro-2H-oxocine-2,5(6H)-dione, a compound identical to the compound of formula (I) except that the double bond between carbons 3 and 4 is in a cis configuration, rather than in a trans configuration as in formula (I).

The compound of formula (I), which we name "Ulocladine" (currently renamed to "Delphiton"), has not been reported before. However, a similar structure has been published previously (J. F. Grove (1964), Metabolic Products of *Stemphylium radicinum*. Part I. Radicinin., Journal of the Chemical Society: 3234-3239; D. C. Aldridge and J. F. Grove, (1964), Metabolic Products of *Stemphylium radicinum*. Part II. (−)-7-Hydroxy-4-oxo-oct-2-enoic Acid Lactone, Journal of the Chemical Society: 3239-3241; B. Lygo and N. O'Conner (1990), Epoxide Ring Opening by Dianions Derived from β-Ketosulphones. Synthetic Studies on the 7-Hydroxy-4-oxopropenoate System and Medium-Ring Lactones, Synlett: 282-284). In these cases, however, it concerns a variant of the molecule in which the double bond is in a cis configuration, i.e. a molecule having the structure of formula (II). A preparation obtained from the fungus *Stemphylium radicinum*, comprising the compound of formula (II), is disclosed to have antagonistic effects toward the fungal plant pathogen *Phytophtora erythroseptica*.

In the compound of formula (I), the double bond between carbons 3 and 4 is in a trans configuration. The J-coupling between the two vinyl protons of 16 Hz as observed with NMR confirmed the trans configuration. In the cis-configuration, the J-coupling would be significantly smaller.

Growth Kinetics of Gram-Positive Bacteria in the Presence of the Compound of Formula (I)

After elucidating the structure, we studied the growth kinetics of several Gram+ bacteria in the presence of 50, 100 and 200 μg/ml of the compound of formula (I), in order to determine whether the compound was bacteriostatic or bactericidal. The bacteria were cultured at 37° C. for 24 hrs

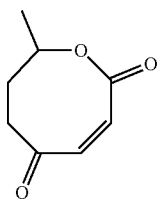

(II)

(with the exception of *Streptococcus pneumoniae* which was cultured until 6 hrs) in the presence of the compound and samples were taken for colony counting at 0, 1, 3, 6 and 24 hrs.

More specifically, bacterial isolates as indicated below were grown on blood-agar plates. Liquid cultures were inoculated in Mueller-Hinton Broth and incubated at 37° C. o/n. The o/n cultures were used to prepare a 0.05-0.1 McFarland suspension in Mueller Hinton Broth, which was incubated at 37° C. until 0.5 McFarland ($1 \times 10^6$ CFU/ml). These suspensions were used to inoculate 5 ml pre-warmed Mueller-Hinton Broth with approximately $1.5 \times 10^5$ CFU/ml with the appropriate antibiotic and antibiotic concentration. Directly after addition of the bacterial suspension a 0.25 ml sample was taken. Further 0.25 ml samples were taken after 1, 3, 6 and 24 hrs. Samples were added to 2.25 ml physiological salt solution. This suspension was used to prepare plates for CFU determination. The lower limit of detection was 40 CFU/ml. Bacterial suspension without antibiotics was checked for normal growth after 24 hrs. Efficient bactericidal activity is defined as at least 3 $\log_{10}$ reduction of CFU.

Figure 2:
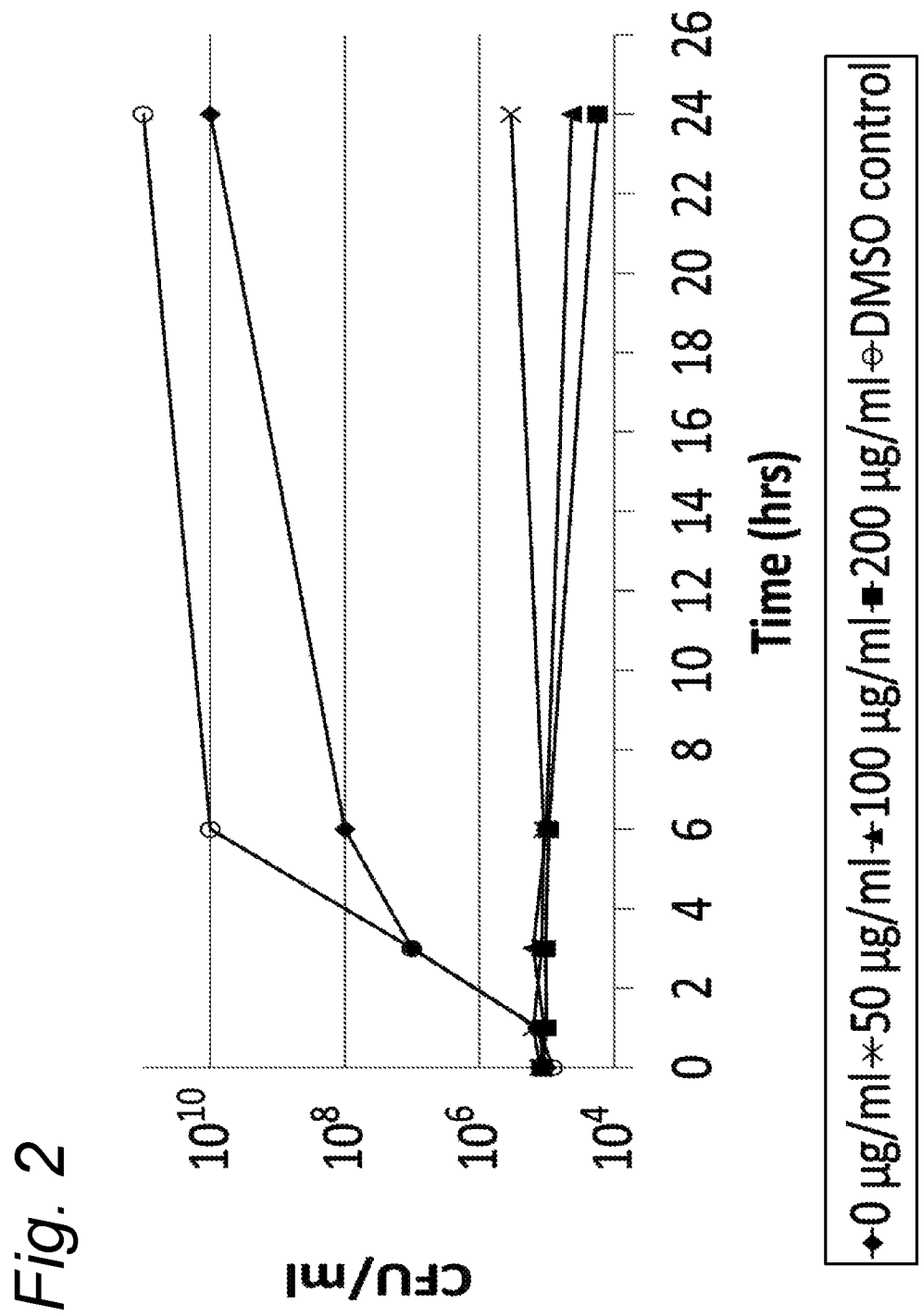
FIG. 2: Growth kinetics of E. faecium (15A623) in the presence of the compound of formula (I).

The bacteria tested were two strains of *Enterococcus faecium* (FIGS. 2A and 2B), MRSA USA300 (FIG. 2C), MSSA (FIG. 2D), *Staphylococcus epidermidis* (FIG. 2E), *Listeria monocytogenes* (FIG. 2F), *Streptococcus* group A (FIG. 2G), *Streptococcus* group B (FIG. 2H) and *Streptococcus pneumoniae* (FIG. 2I).

Based on these time-kill curves, we can conclude that the compound of formula (I) is bacteriostatic on *Streptococcus* Group B and on both *Enterococcus faecium* strains but that the compound is bactericidal on MRSA USA300, *Staphylococcus epidermidis*, MS SA, *Streptococcus* Group A, *Streptococcus pneumoniae* and *Listeria monocytogenes*.

Hydrogenation Inactivates the Antibacterial Activity of the Compound of Formula (I)

Figure 3:
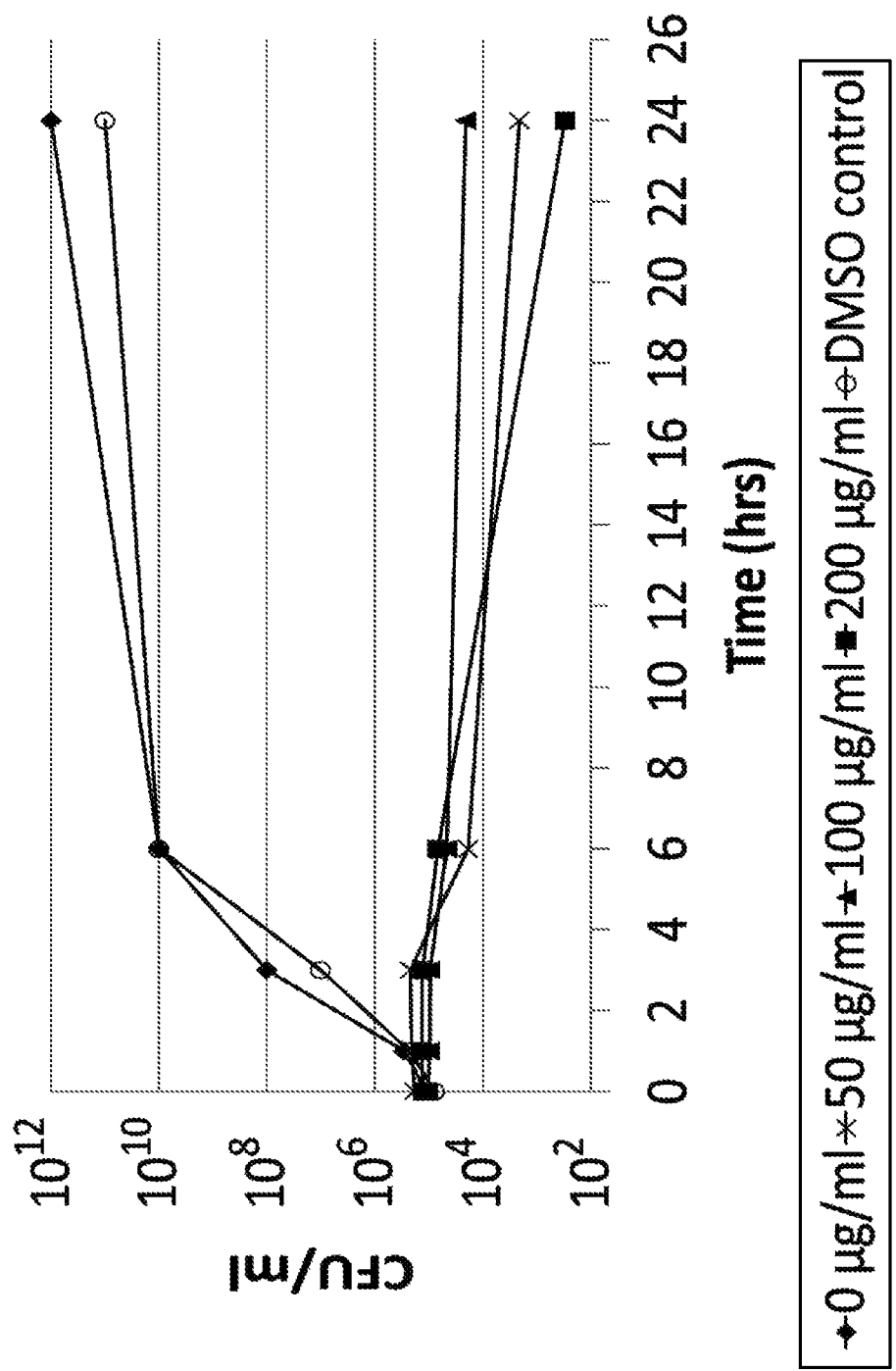
FIG. 3: Growth kinetics of E. faecium (16D030) in the presence of the compound of formula (I).
Figure 4:
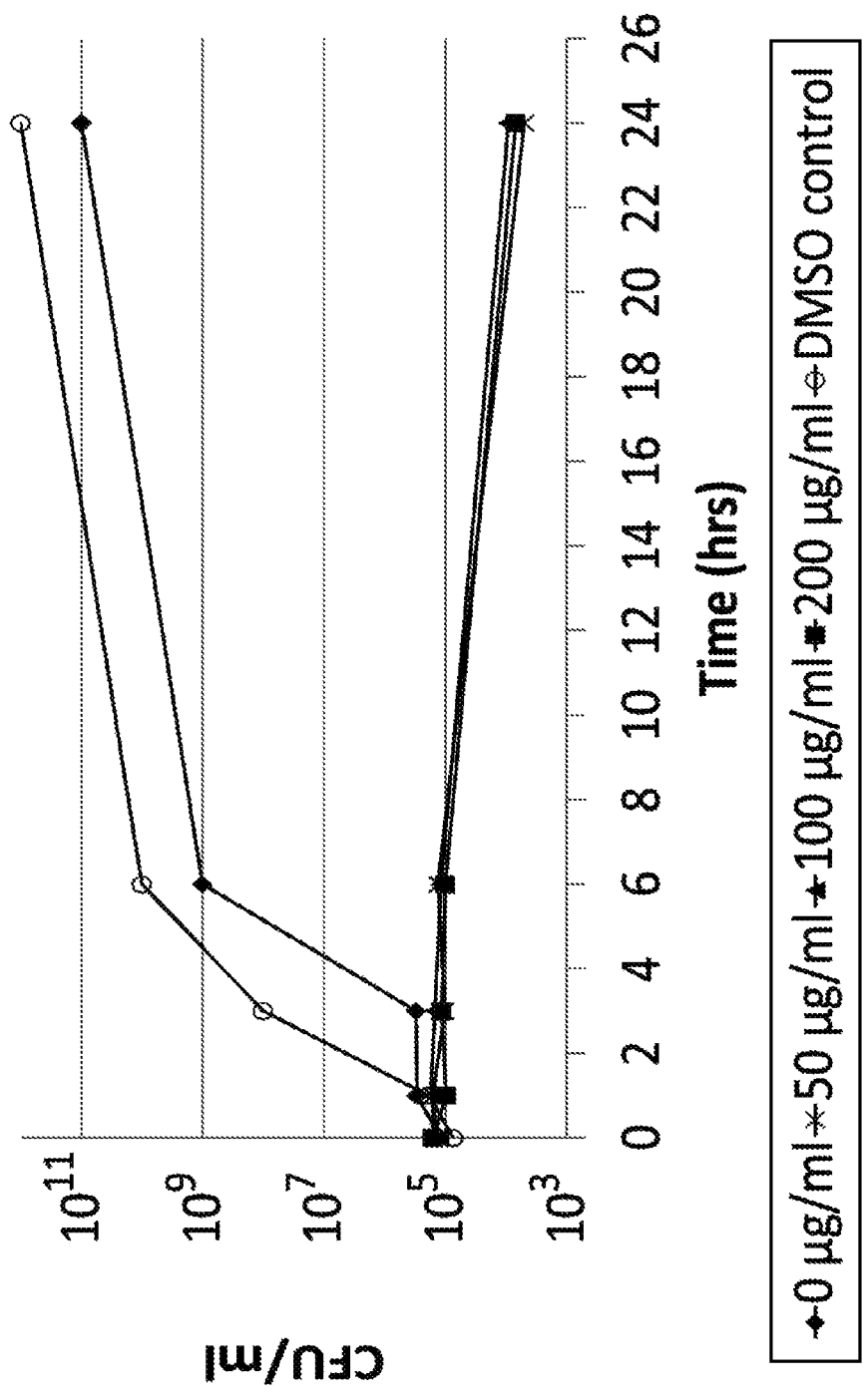
FIG. 4: Growth kinetics of MRSA USA300 in the presence of the compound of formula (I).
Figure 5:
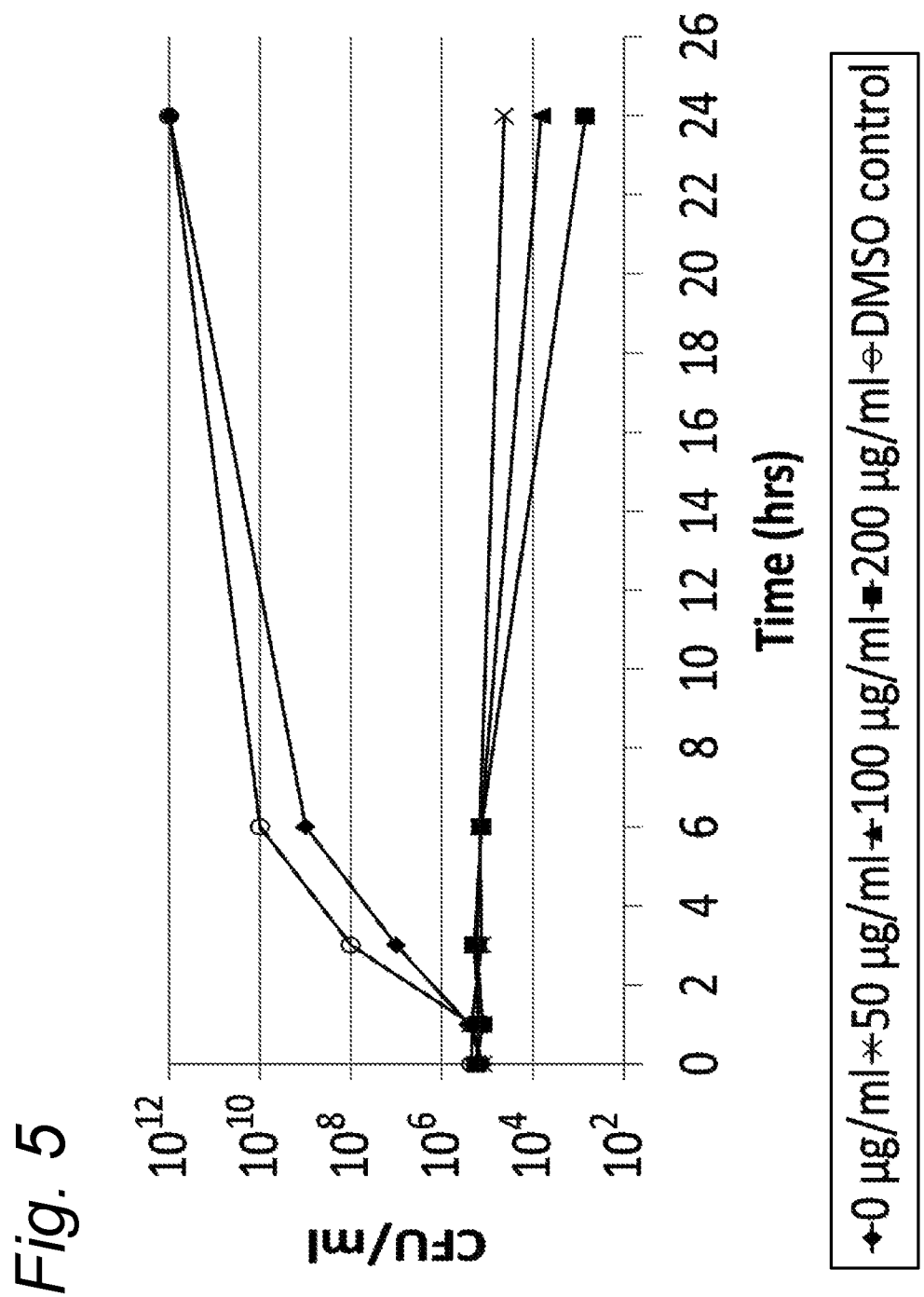
FIG. 5: Growth kinetics of MSSA in the presence of the compound of formula (I).
Figure 6:
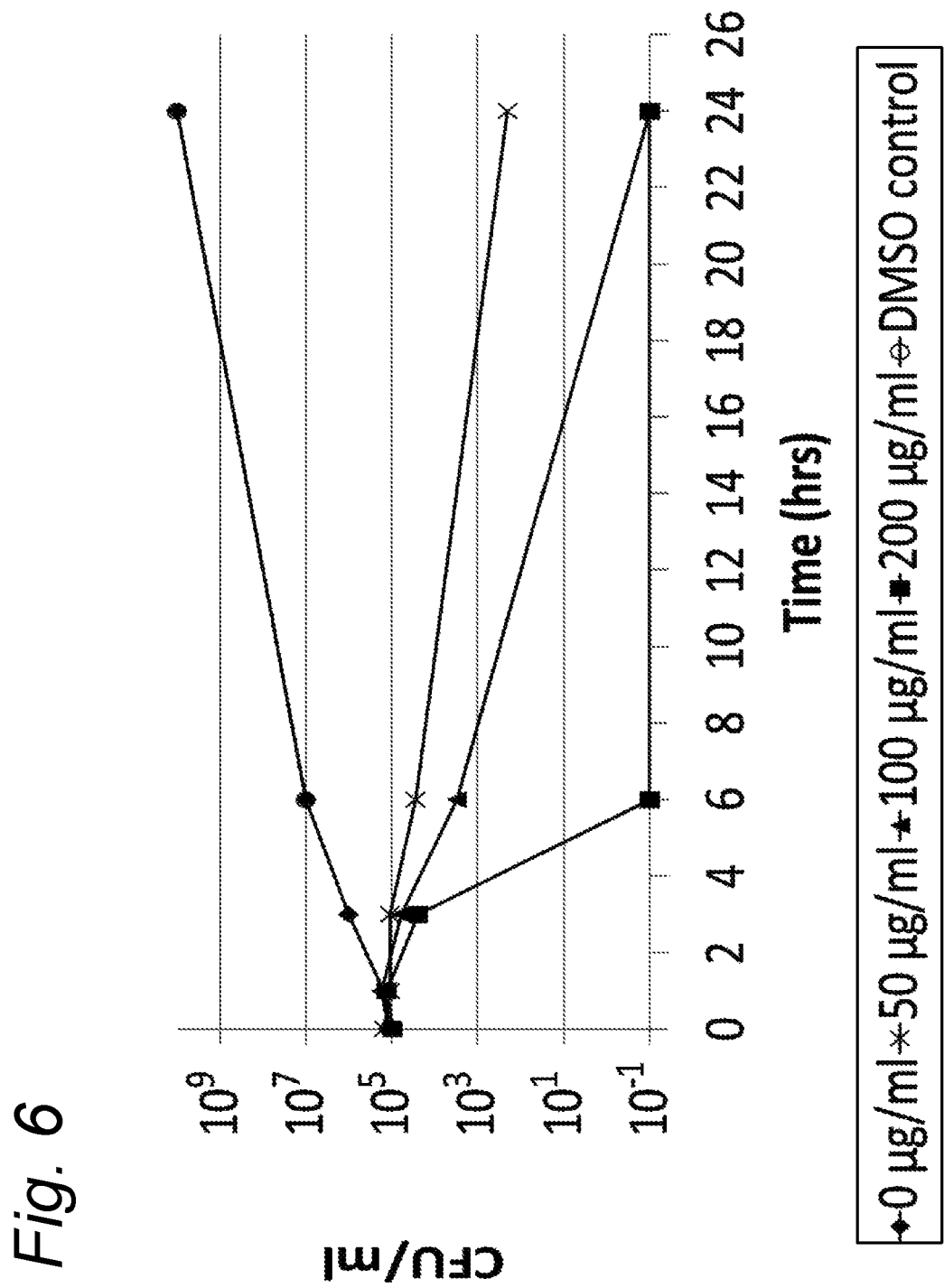
FIG. 6: Growth kinetics of S. epidermidis in the presence of the compound of formula (I).
Figure 7:
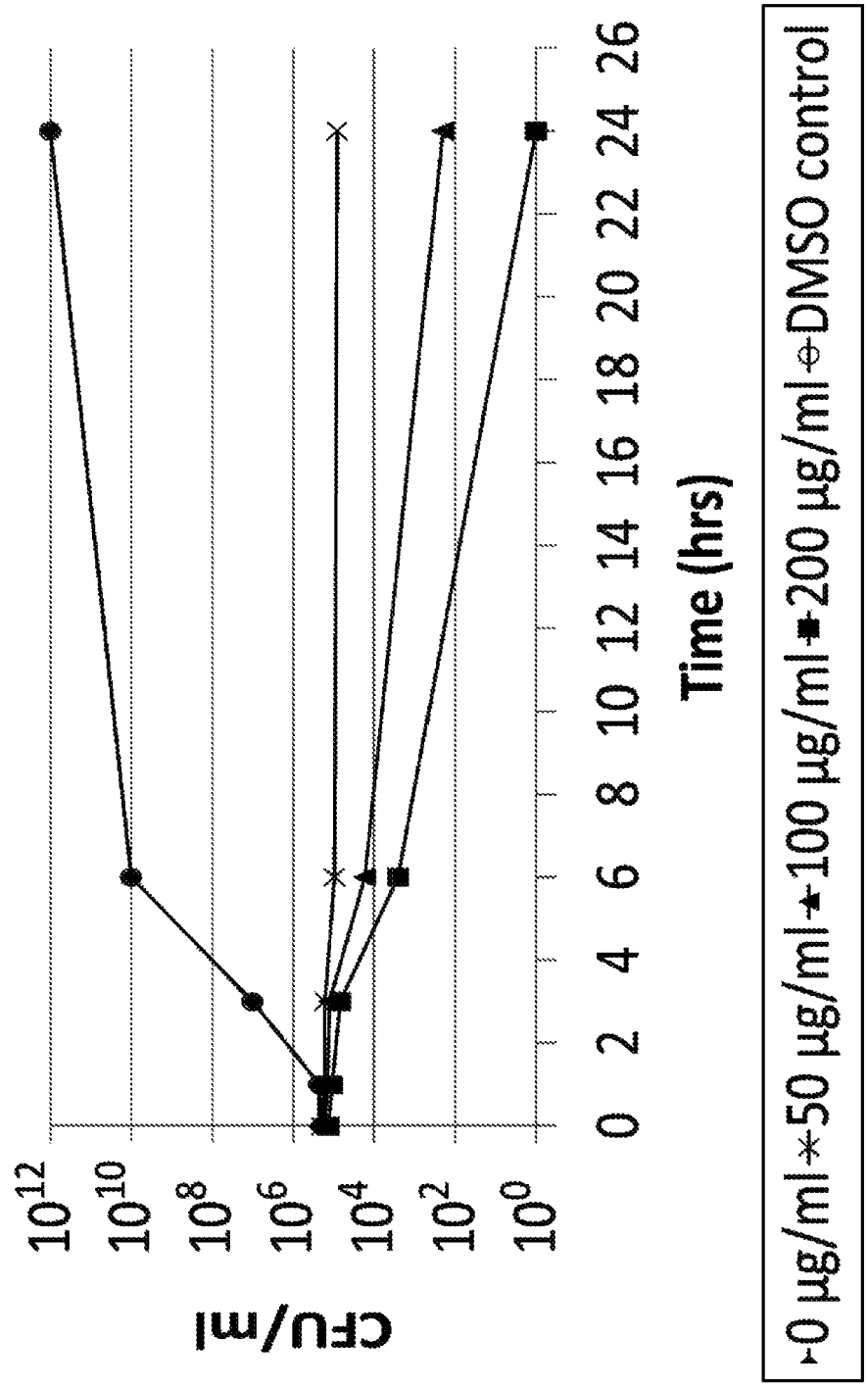
FIG. 7: Growth kinetics of Listeria monocytogenes in the presence of the compound of formula (I).
Figure 8:
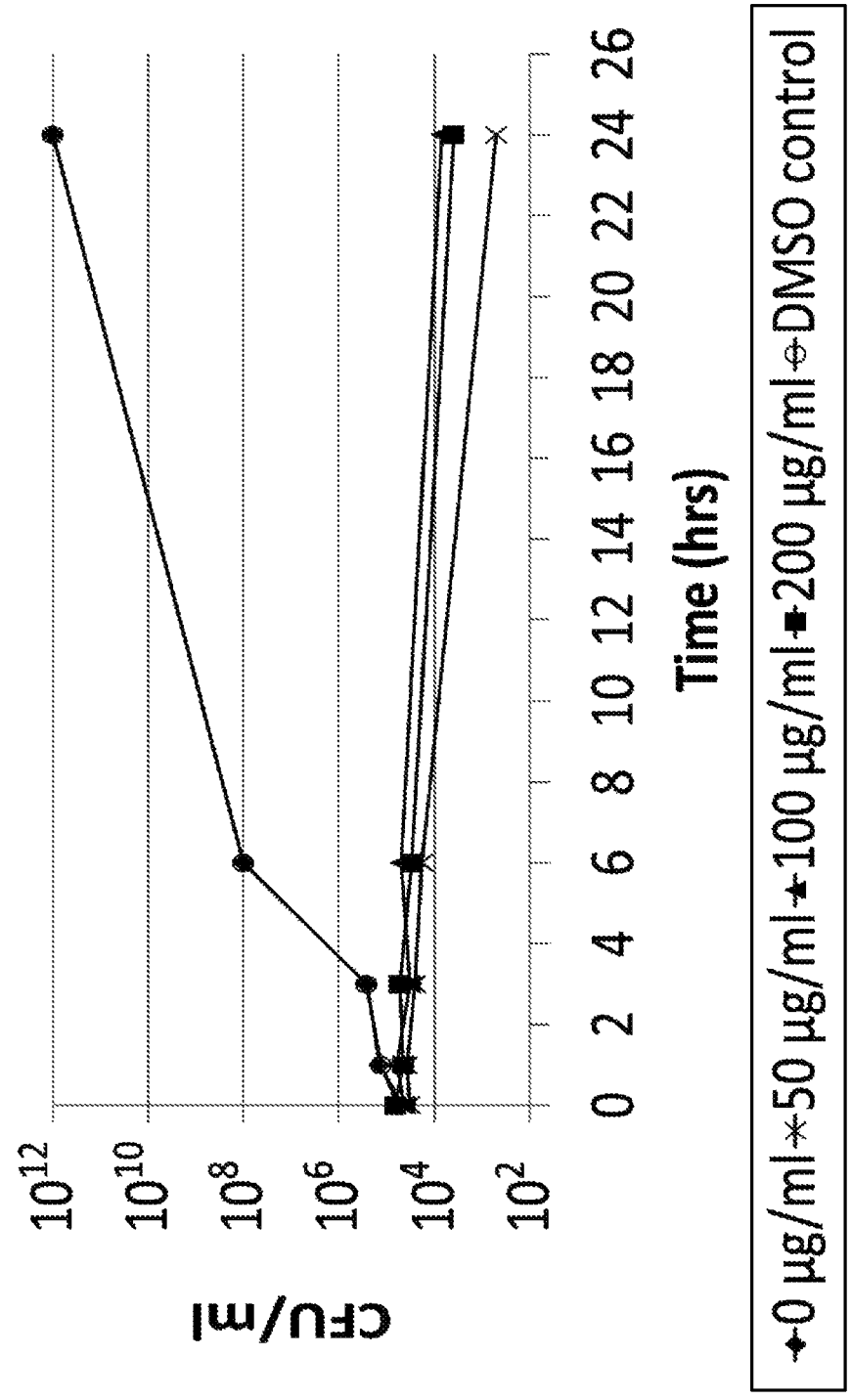
FIG. 8: Growth kinetics of Streptococcus group A in the presence of the compound of formula (I).
Figure 9:
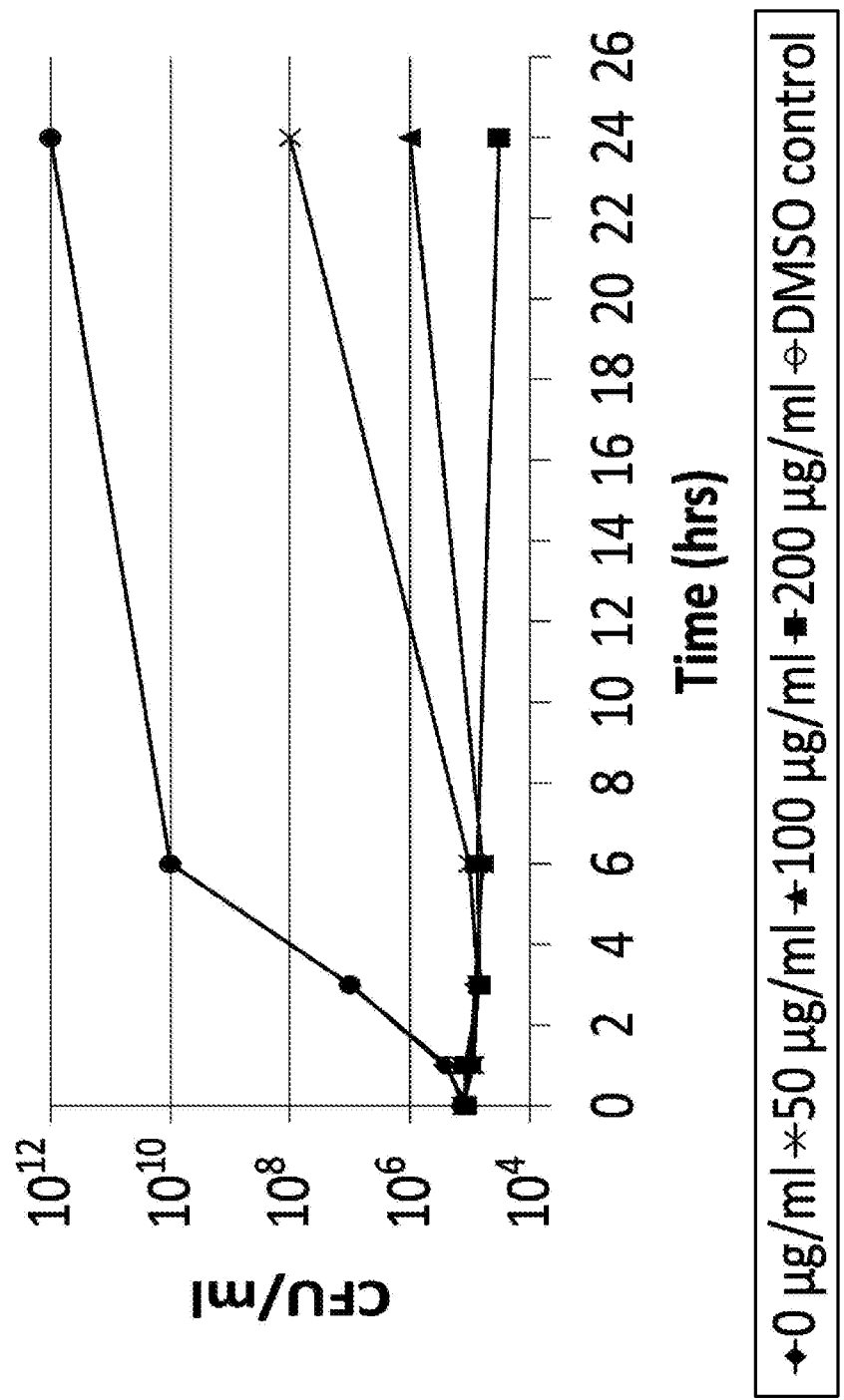
FIG. 9: Growth kinetics of Streptococcus group B in the presence of the compound of formula (I).
Figure 10:
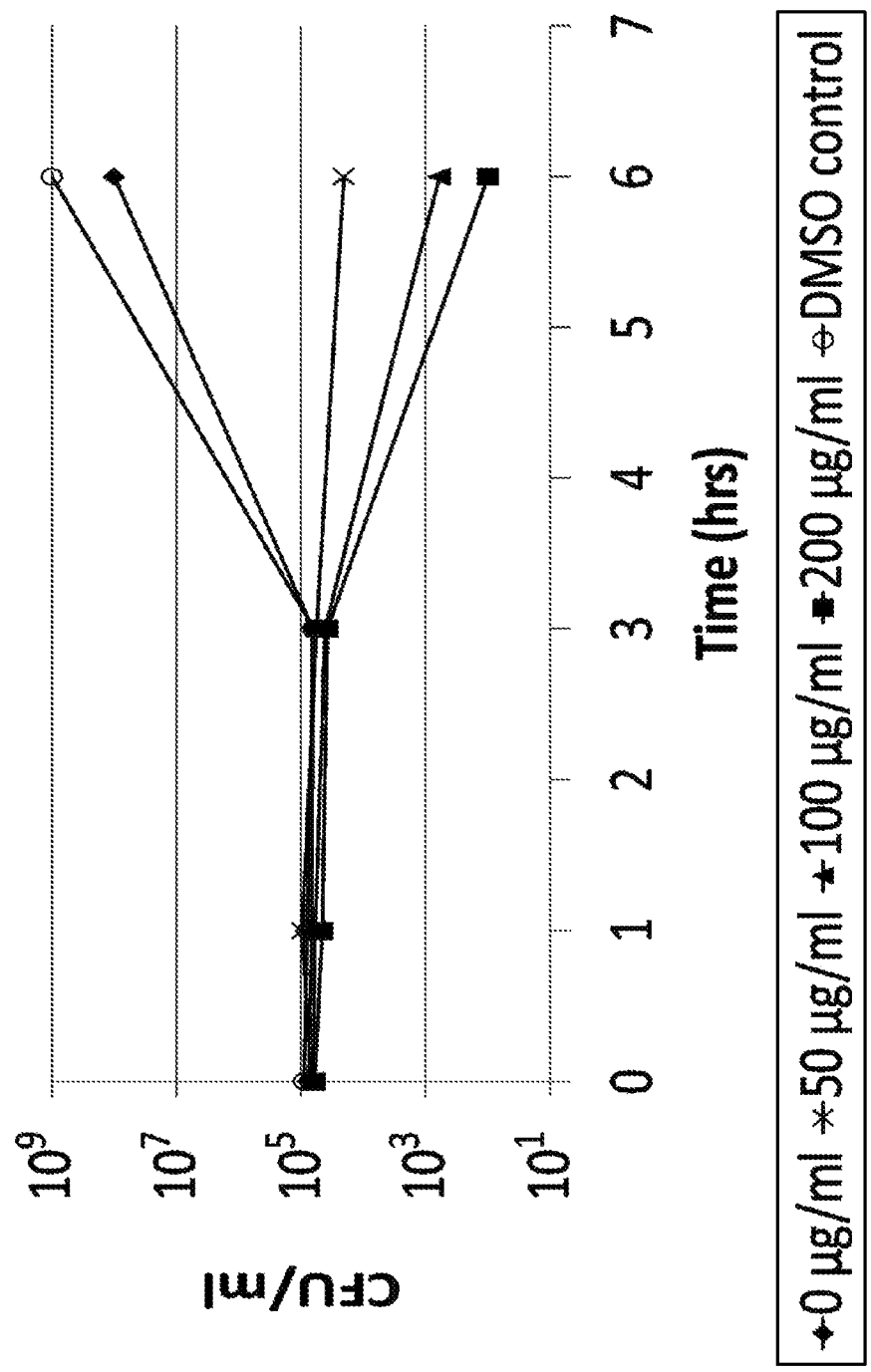
FIG. 10: Growth kinetics of Streptococcus pneumoniae in the presence of the compound of formula (I).
Figure 11:
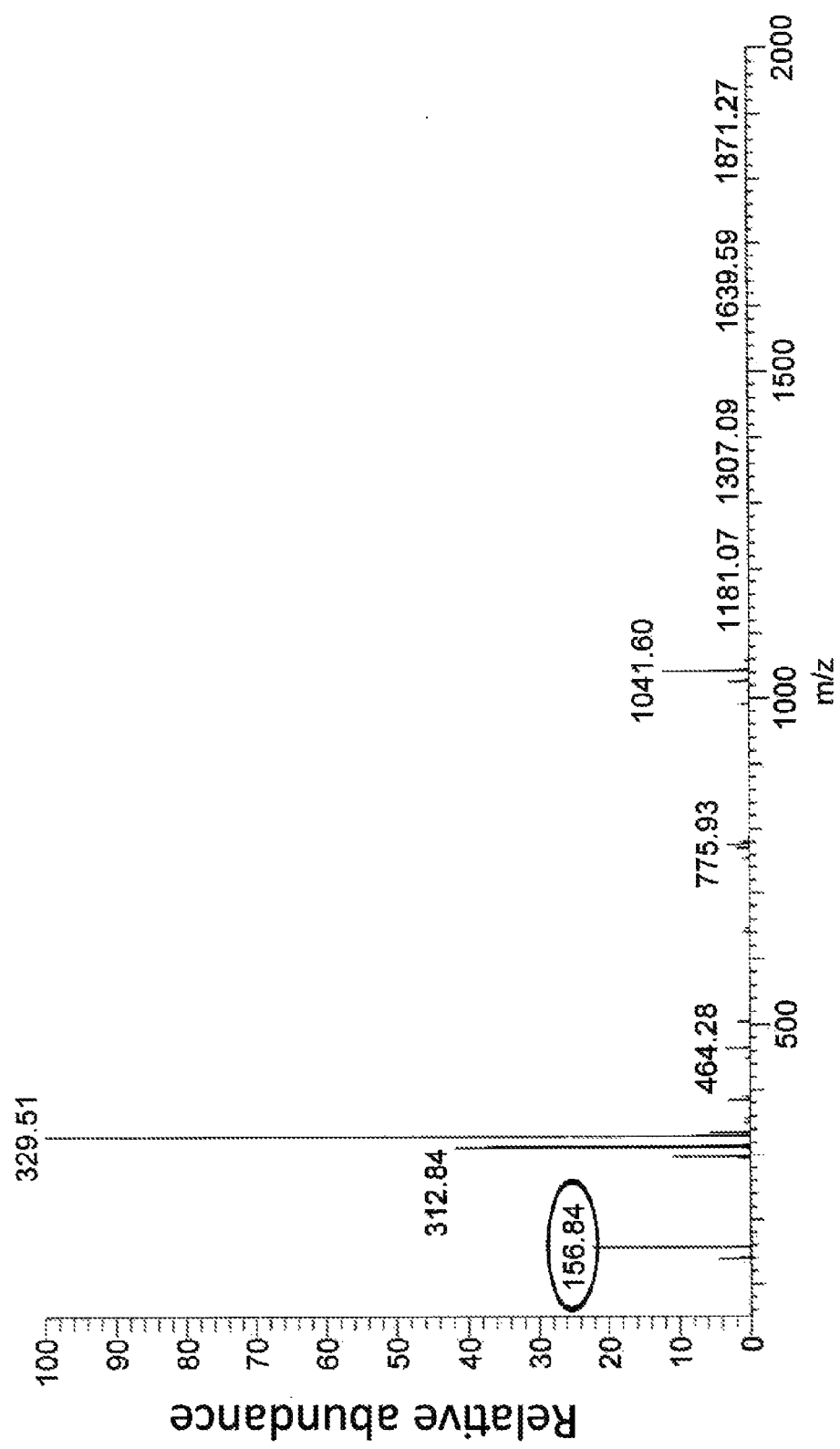
FIG. 11: LC-MS spectrum of the hydrogenated derivative of the compound of formula (I) (2690-f49-hydro). The mass the compound of formula (I)+2 is indicated in the circle.

The trans configuration of the double bond in the compound of formula (I) is unique and generates a highly reactive moiety, a Michael acceptor for nucleophilic attack. We hypothesized that this was the active core that was responsible for the antibacterial activity. In an approach to confirm the importance of the trans-configuration of the double bond, we hydrogenated the double bond. The hydrogenation reaction was done as previously described by Aldrige and Grove (1964, supra). Briefly, the compound was dissolved in ethyl acetate and was hydrogenated in the presence of 5% palladium-carbon for 96 h. The product was filtered and the ethyl acetate was evaporated off. The residue was then dissolved in acetonitrile and analyzed by analytical HPLC to check the purity. The hydrogenated sample, named 2690-f49-hydro, was also analyzed by LCMS, which revealed the exact mass of the compound of formula (I)+2 (156.84) (FIG. 3), as expected. A $^1$H-NMR spectrum was measured, wherein the absence of peaks for the vinyl protons between 7 and 8 ppm, confirmed that the double bond in the compound of formula (I) was saturated (data not shown). To estimate the relative concentration of the hydrogenated sample, a standard addition experiment was performed with the compound of formula (I) and 2690-f49-hydro on analytical HPLC. The area under the peaks of both samples were roughly the same (data not shown), suggesting equal concentrations of the compound of formula (I) and its hydrogenated derivative 2690-f49-hydro. The compound of formula (I) was active against *E. faecium* (15A623), whereas its hydrogenated derivative 2690-f49 hydro, at similar concentrations, was not active. Even at 16-fold higher concentrations, 2690-f49 hydro was not active against *E. faecium* (15A623). We conclude that the double bond is required for antibiotic activity of the compound of formula (I).

TABLE 4

| | Apparatus | |
|---|---|---|
| | Apparatus | Column |
| Prep. HPLC | LC-MS QP8000 prep: Shimadzu<br>Piston pump: Shimadzu LC-8A<br>UV-VIS detector: Shimadzu SPD-10A (standard 214 nm and 254 nm)<br>Fraction collector: Gilson Liquid Handler 215 | Reprosil-PurC18 AQ;<br>250 × 22 mm; Screening Device R10.AQ.S2522<br>Particle size: 10 μm<br>Pore size: 120 Å<br>Carbon load: 15%<br>pH range: 1-10 |
| Analytical HPLC | VP SHIMADZU<br>System controller: SCL-10A<br>Pump: LC-10AT<br>UV-VIS detector: SPD-10A (standard 214 nm and 254 nm)<br>Auto injector: SIL-10AD (sample loop 50 μl) | Reprosil-PUR C18 AQ;<br>250 × 4.6 mm; Screening Device R15.AQ.S2546<br>Particle size: 5 μm<br>Pore size: 120 Å<br>Carbon load: 15%<br>pH range: 1-10 |
| LC-MS | VP SIMADZU<br>Column oven: CTO-10AS<br>System controller: SCL-10A<br>Pump: LC-10AD<br>UV-VIS detector: SPD-10A (standard 214 nm and 254 nm)<br>Auto injector: SIL-10AD (sample loop 50 μl)<br>MS: Finnigan LCQ Deca XP Max | Reprosil-PurC18 AQ;<br>250 × 22 mm; Screening Device R10.AQ.S2522<br>Particle size: 10 μm<br>Pore size: 120 Å<br>Carbon load: 15%<br>pH range: 1-10 |

The invention claimed is:

1. A method for producing a compound comprising an (E)-7-hydroxy-4-oxo-hept-2-enoic acid lactone ring, the method comprising:
   (a) culturing a fungus of the fungal Family of Pleosporaceae of the genus *Ulocladium*, in a medium conducive to the production of the compound; and,
   (b) optionally recovery of the compound.

2. The method according to claim 1, wherein the culturing is at a temperature less than 30° C.

3. The method according to claim 1, wherein the compound is recovered by solvent extraction.

4. The method according to claim 3, wherein the solvent is ethyl acetate.

* * * * *